United States Patent
Clüsserath

(10) Patent No.: US 10,053,251 B2
(45) Date of Patent: Aug. 21, 2018

(54) METHOD FOR STERILIZING PACKAGING

(71) Applicant: KHS GmbH, Dortmund (DE)

(72) Inventor: Ludwig Clüsserath, Bad Kreuznach (DE)

(73) Assignee: KHS GmbH, Dortmund (DE)

(*) Notice: Subject to any disclaimer, the term of this patent is extended or adjusted under 35 U.S.C. 154(b) by 15 days.

(21) Appl. No.: 15/103,060

(22) PCT Filed: Nov. 27, 2014

(86) PCT No.: PCT/EP2014/075752
§ 371 (c)(1),
(2) Date: Jun. 9, 2016

(87) PCT Pub. No.: WO2015/086329
PCT Pub. Date: Jun. 18, 2015

(65) Prior Publication Data
US 2016/0376046 A1  Dec. 29, 2016

(30) Foreign Application Priority Data
Dec. 10, 2013 (DE) .................. 10 2013 113 784

(51) Int. Cl.
*B65B 55/10* (2006.01)
*B65B 55/08* (2006.01)
*A61L 2/025* (2006.01)
*A61L 2/08* (2006.01)
*A61L 2/10* (2006.01)
(Continued)

(52) U.S. Cl.
CPC .............. *B65B 55/08* (2013.01); *A61L 2/025* (2013.01); *A61L 2/087* (2013.01); *A61L 2/10* (2013.01); *A61L 2/16* (2013.01); *A61L 2/18* (2013.01); *A61L 2/20* (2013.01); *B65B 55/10* (2013.01); *A61L 2202/23* (2013.01)

(58) Field of Classification Search
CPC . B65B 55/08; B65B 55/10; A61L 2/16; A61L 2/20; A61L 2/18; A61L 2/087; A61L 2/025; A61L 2/10
See application file for complete search history.

(56) References Cited

U.S. PATENT DOCUMENTS 2,380,984 A    8/1945   Moeller
6,164,044 A *  12/2000  Porfano ................ A61M 5/001
                                                    422/28
(Continued)

FOREIGN PATENT DOCUMENTS

CN    102826261     12/2012
DE    196 44 251    4/1998
(Continued)

OTHER PUBLICATIONS

English translation of CN102826261, Dec. 19, 2012.*

Primary Examiner — Regina M Yoo
(74) Attorney, Agent, or Firm — Occhiuti & Rohlicek LLP

(57) ABSTRACT

Disinfecting a surface of packaging includes breaking up one of an outer covering and a membrane of germs on the surface, and applying carbon dioxide to the surface. Breaking up the outer covering or membrane is carried out by one or more of applying bactericidal energy, illuminating with UV radiation, illuminating with ultrasonic radiation, applying a bactericidal treatment medium, and applying a chlorine compound.

12 Claims, 3 Drawing Sheets

(51) Int. Cl.
*A61L 2/18* (2006.01)
*A61L 2/20* (2006.01)
*A61L 2/16* (2006.01)

(56) References Cited

U.S. PATENT DOCUMENTS

| | | | |
|---|---|---|---|
| 6,189,292 B1 * | 2/2001 | Odell | A61M 5/001 141/1 |
| 6,250,052 B1 * | 6/2001 | Porfano | A61M 5/001 53/425 |
| 7,067,089 B2 | 6/2006 | Wen | |
| 2009/0134338 A1 | 5/2009 | Eguchi | |

FOREIGN PATENT DOCUMENTS

| | | |
|---|---|---|
| DE | 10 2008 031 369 | 1/2010 |
| DE | 10 2010 044244 | 3/2012 |
| DE | 10 2011 107 772 | 1/2013 |
| DE | 20 2012 011 289 | 1/2013 |
| EP | 0 341 069 | 11/1989 |
| WO | WO2013/054539 | 4/2013 |

* cited by examiner

METHOD FOR STERILIZING PACKAGING

RELATED APPLICATIONS

This is the national stage, under 35 USC 371, of PCT/EP2014/075752, filed on Nov. 27, 2014, which claims the benefit of the Dec. 10, 2013 priority date of German application DE 10 2013 113784.9, the contents of which are herein incorporated by reference.

FIELD OF INVENTION

The invention relates to packaging of products, and in particular, to disinfection of packages.

BACKGROUND

In the packaging of products, it is frequently necessary to disinfect or sterilize surfaces that convey the products or filling contents. These surfaces include surfaces that come in contact with a product or filling contents, surfaces of packaging and packaging closure elements, and machine surfaces that come in contact with a product or filling contents and/or with a treatment medium or treatment means introduced into the packaging during filling. This is particularly important so as kill germs. These include germs that are harmful to the product, such as fungi, bacteria, viruses, etc.

A known method for carrying out such a procedure is to use a suitably powerful disinfection agent.

SUMMARY

An object of the invention is to provide a particularly effective method for the disinfection or sterilization of surfaces of product-critical or filling contents-critical surface areas of packaging.

As used herein, "packaging" signifies packages or containers that are conventionally used in the food sector, and in particular also in the beverage sector, and specifically, in particular, containers such as bottles, cans, or kegs, made of glass, plastic, metal, or also soft packaging, such as that made from cardboard and/or plastic film and/or metal film or foil.

As used herein, "product-critical or filling contents-critical surfaces" include surfaces that come into contact or are in contact with a product or filling contents, in particular inner surfaces of packaging and/or packaging closure elements, but also surfaces formed in machines and systems with which the respective product or filling means come in contact or are in contact, at least for a limited period of time, such as, for example, the inner surfaces of product or filling contents tanks, product or filling contents pipes, filling elements, etc. "Product-critical or filling contents-critical surfaces" in the meaning of the invention are, however, also such surfaces, in particular in systems and machines, which come in contact or are in contact with a medium, at least for a limited period of time, which are used as operational means during the filling of the packaging, which are introduced into the packaging, for example as flushing gas or as tensioning gas during the pressure filling of bottles or similar containers.

As used herein, "pressure filling" is to be understood in general to mean a filling process with which the container to be filled in each case is subjected to pre-tension before the actual filling with a tensioning gas (inert gas or CO2 gas) under pressure, which then, during the filling, is increasingly forced out of the interior of the container, as return gas, by the filling content that flows in.

A particular feature of the method according to the invention is that the treatment of the surface that is to be disinfected, with the disinfection agent, is supported by the imposition of an anti-bacterial energy application and/or with an anti-bacterial treatment medium. In this situation, with this anti-bacterial energy application and/or with this anti-bacterial treatment medium, the cell structure, in particular outer coverings or membranes of the germs are broken up, as a result of which an improved and more rapid penetration of the disinfection agent into the germs is achieved, and the quality of the disinfection, i.e. the disinfection rate, is improved, with reduced treatment duration.

The energy application is provided by light, preferably UV light or UV radiation, by light flashes, by ultrasonic waves, by electromagnetic radiation, and/or by electron radiation.

Suitable as anti-bacterial treatment media are, for example, chlorine compounds, such as chlorine oxide ($ClO_2$) or a medium containing these chlorine compounds as effective components.

As a disinfection agent, or as an effective, i.e. bactericidal component of the disinfection agent, a component may be used that is environmentally compatible and, in particular, that also avoids the risk of injury to the operating personnel, such as carbon dioxide ($CO_2$), and/or the disinfection agent can contain the bactericidal component, such as a chlorine compound, preferably chlorine dioxide ($ClO_2$) in an only reduced dosage, for example in a dosage reduced in comparison with the bactericidal treatment medium.

The disinfection agent, as well as the anti-bacterial treatment medium are used, with the method according to the invention, either in the form of gas and/or vapor, or also in liquid form, for example as an aqueous solution.

As used herein, expressions such as "essentially" or "approximately" include deviations from an exact value by ±10%, preferably by ±5%, and/or deviations in the form of changes that are not of significance to the function.

Further embodiments, advantages, and possible applications of the invention are also derived from the following description of exemplary embodiments and from the figures. In this situation, all the features described and/or represented as images are individually or in any desired combination basically the object of the invention, regardless of their inclusion in the claims or reference made to them. The contents of the claims are also a constituent part of the description.

BRIEF DESCRIPTION OF THE FIGURES

The invention is explained in greater detail hereinafter by exemplary embodiments on the basis of the figures, in which.

DETAILED DESCRIPTION

Figure 1:
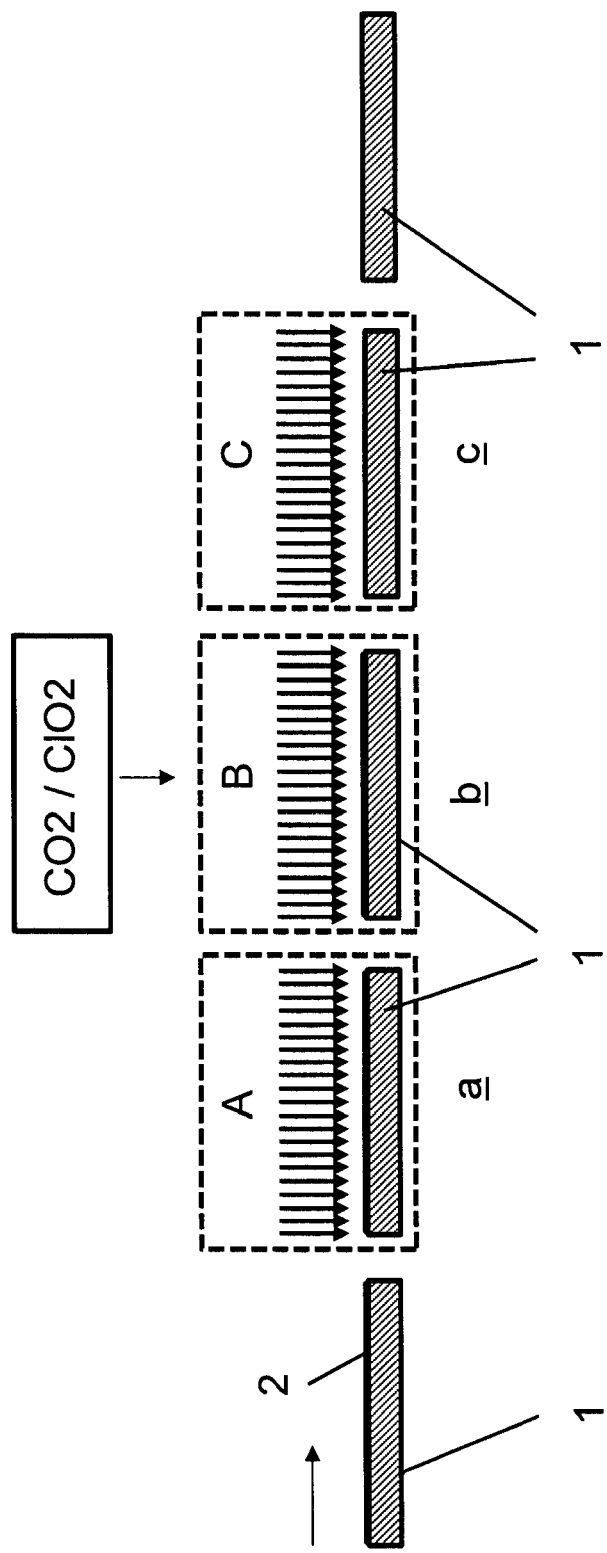
FIG. 1 shows a sequence of different method steps for the disinfection or sterilization of surfaces, in particular of surfaces conveying product or filling contents.

FIG. 1 shows an object 1 that, during its use, comes in contact with at least one surface 2 with a product of filling contents, such as a beverage, and for this reason must be disinfected or sterilized at least on this surface 2. The object 1 is reproduced only schematically and in part representation, Examples of an object 1 include a container that is to be filled with a product or filling contents, e.g. a beverage, a container closure element, or a function element of a container treatment machine, wherein, in this case, the surface 2 forms a machine surface that is in contact or comes in contact with the product or filling contents or with an operating means.

Figure 2:
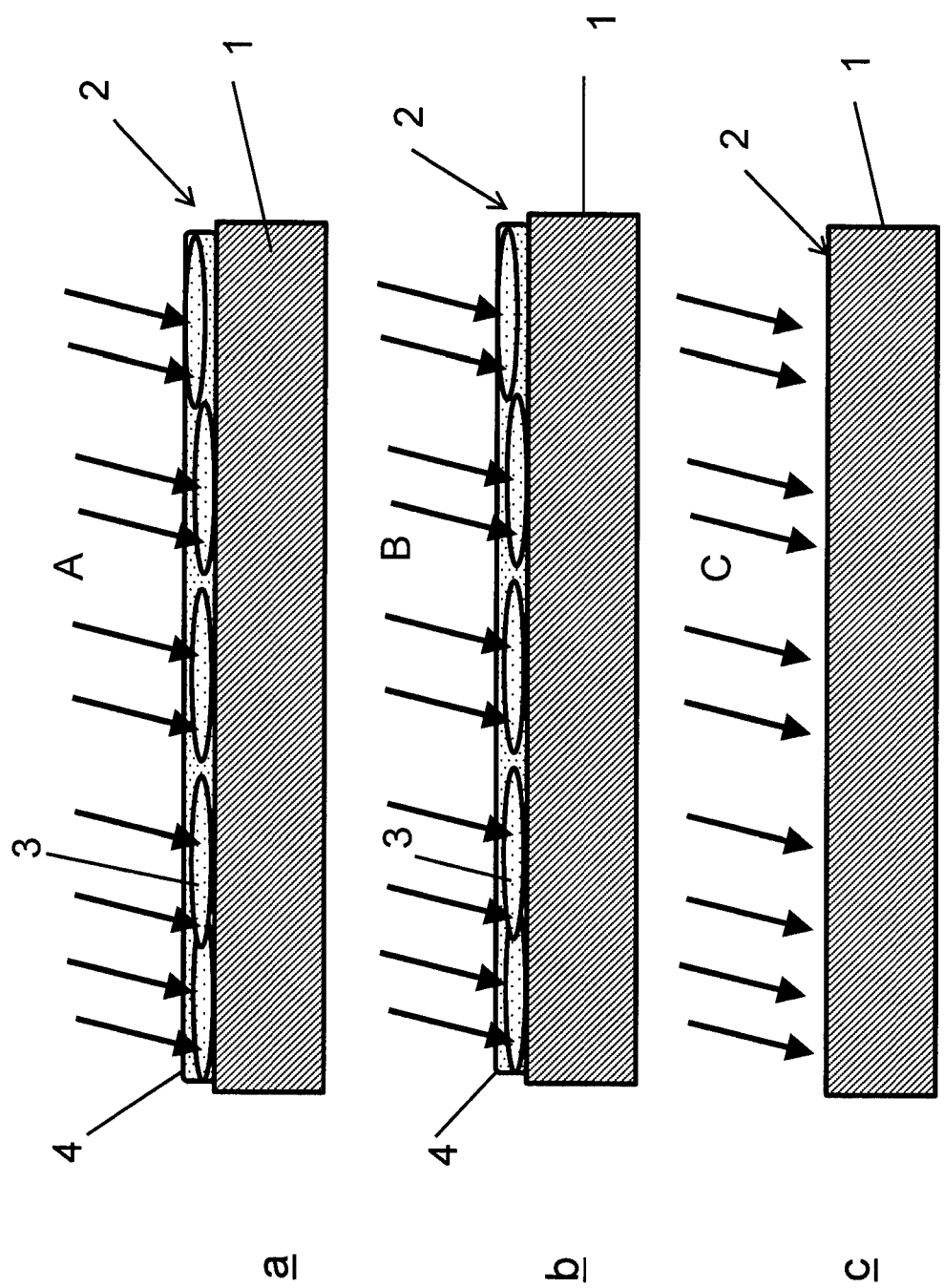
FIG. 2 shows, in the diagrams a-c, again in an enlarged representation, a surface during the treatment with the method from FIG. 1.

Diagram a of FIGS. 1 and 2 shows a first step for disinfection or sterilization of the surface 2. The first step includes subjecting the surface 2 to an aggressive anti-bacterial treatment medium. Examples of ways to execute the first step include any one or more of: exposure to chlorine dioxide ($ClO_2$); exposure to radiative energy A, such as electromagnetic radiation, including light and in particular UV light, either continuously or in flashes, exposure to ultrasonic radiation, and exposure to electron radiation. This treatment promotes damage to germs, and in particular, to their cell structure, especially the cell wall or membrane of germs adhering to the surface 2. It also reaches a surface layer 4 containing these germs 3. The anti-bacterial treatment medium is applied, for example, in gas form and/or in an aqueous solution, for example by metering nozzles, onto the surface 2.

The treatment can be applied both by energy application as well as by the imposition of the anti-bacterial treatment medium on the surface 2. The two treatments can be applied with time delay, simultaneously, or with temporal overlap.

After the damaging or breaking up of the germs 3, corresponding to diagram b in FIGS. 1 and 2, a further method step of treating the surface 2 with the disinfection agent takes place. By contrast with known methods for disinfection and/or sterilization of containers, container closure elements, and/or machine surfaces with a disinfection agent, the method disclosed herein permits a particularly gentle, environmentally-friendly, and/or machine-friendly disinfection agent to be used. This also avoids the risk of injuring operating personnel. This is possible due to the fact that in method step a, the germs 3 or their cell structures or cell membranes respectively, as well as also the layer 4, have already been damaged or broken up to the extent that, in method step b, a gentle disinfection agent is sufficient for the reliable killing of the previously damaged germs 3. In this situation, it is possible to achieve a killing rate that, using conventional methods, can only be achieved with a very intensive disinfection agent.

A suitable disinfection agent for method step b is carbon dioxide ($CO_2$), the bactericidal effect of which arises from the way it reduces pH value as it penetrates the germs 3. Eventually, the germ can no longer regulate itself and dies.

Another suitable disinfection agent for method step b is chlorine dioxide ($ClO_2$) at a dosage lower than that used in method step a.

The disinfection agent is applied to the surface 2 in method step b as either a gas or in the form of an aqueous solution, as is indicated with the arrows B. In those practices that use $CO_2$ in an aqueous solution as a disinfection agent, the solution contains $CO_2$ in a concentration of, for example, up to 2.5 grams per liter of water at ambient or atmospheric pressure.

Due to the damaging of the germs 3 and due to the breaking up of the surface layer 4 in the first step a, the second step b achieves a reliable disinfection and sterilization also takes place of those regions of the surface 2 that, in the first step a, were shadowed. These shadowed regions were either not pre-treated by the energy application in the first step, or were treated inadequately. These shadowed regions make up only a minor part in terms of surface area. In most cases, the shadowed regions take up less than 20% of the surface's total surface.

In a third method step, corresponding to diagram c in FIGS. 1 and 2, there takes place preferably a flushing of the surface 2, and therefore a complete removal of the killed germs 3 and of the surface layer 4, with a suitable flushing medium C. A suitable flushing medium would be sterile water.

It has been assumed heretofore that the object 1 is treated only on one surface 2 for the disinfection or sterilization. It is understood that the treatment is applied to all the surfaces 2 of the respective object 1 that must be sterile or germ-free. The first through third steps a-c described heretofore are then carried out on all the surfaces.

It has also been assumed heretofore that the energy application is effected directly onto the surface 2 that is to be disinfected or sterilized. In principle, with objects 1 that are permeable to the energy radiation used, which can be light, ultraviolet radiation, electromagnetic radiation generally, or electron radiation, it is also irradiate the surface 2 that is to be disinfected or sterilized with this energy, in addition to irradiating the object 1.

If the objects 1 are containers, then the method described herein is carried out, for example in a system or machine for the cleaning and/or sterilization of the containers, for example in a rinsing machine. In these practices, nozzles direct the bactericidal treatment medium and the disinfection medium into the containers or onto the inner surfaces of the containers that are to be disinfected or sterilized. If the objects 2 are container closure elements, then this method is carried out, for example, in a system or a system component that provides a closing machine with the sterilized container closure elements.

Figure 3:
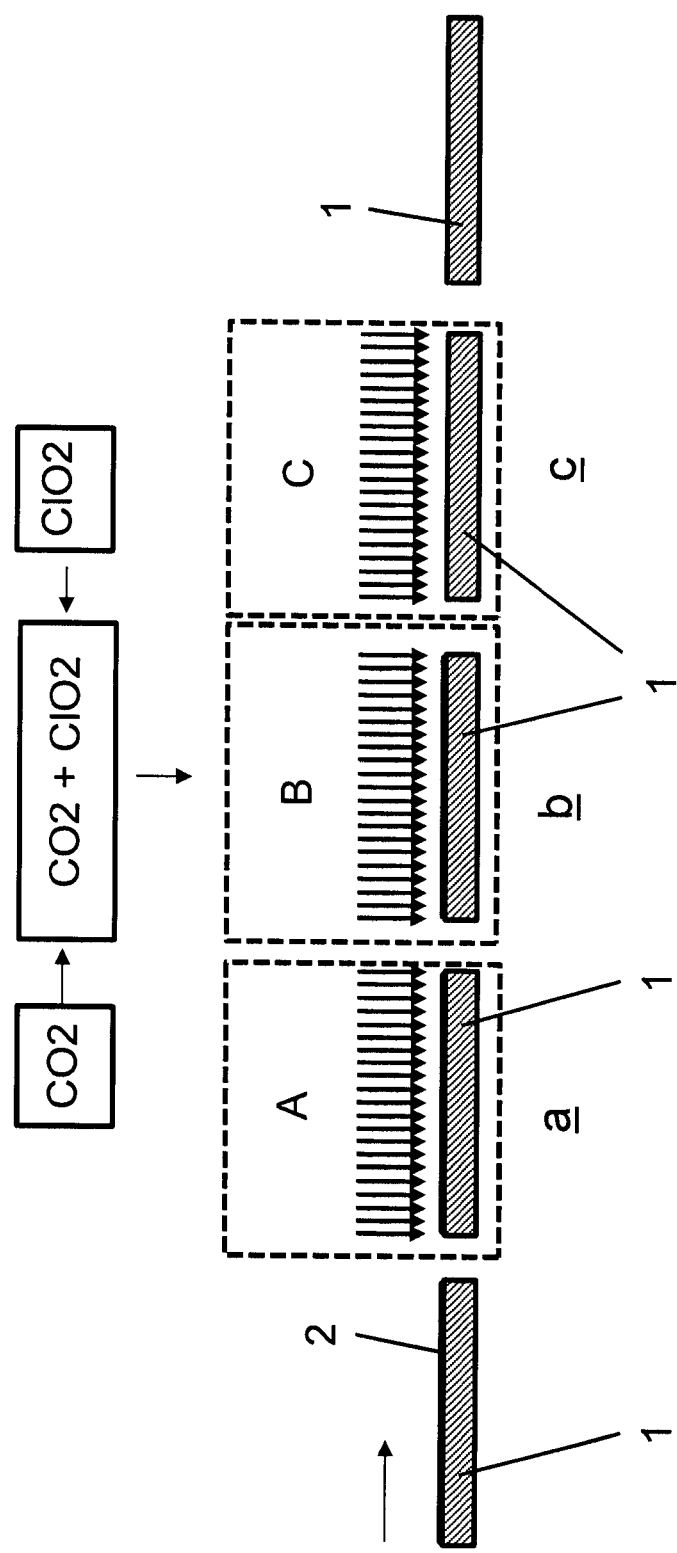
FIG. 3 shows a representation similar to FIG. 1 with a further embodiment of the method according to the invention.

FIG. 3 shows, in diagrams a-c, the method steps of a further method according to the invention that differs from the method described in connection with FIG. 1 only in that, during the disinfection, i.e. the second step b, the disinfection agent contains at least two components in mixture. An example of such a mixture is a mixture of $ClO_2$ and $CO_2$. The two components of the disinfection agent are provided pre-mixed or pre-metered in an aqueous solution or in a gas, and applied onto the surface 2 that is to be disinfected or sterilized.

To avoid the inadvertent release of a gas component of the mixture, such as carbon dioxide, it is useful to keep the disinfection agent under pressure during the metering and up until its application onto the surface 2. Doing so prevents the escape of the mixture's gaseous constituents. This ensures that the mixture retains its full effectiveness until it actually emerges from a treatment nozzle and enters an environment at ambient pressure. This pressurization technique promotes a higher bactericidal rate with reduced treatment duration because the effectiveness of the disinfection agent is fully retained.

Regardless of whether the disinfectant agent formed from at least two components is applied in gaseous form or in liquid form, for example as an aqueous solution, onto the surface 2, it is also possible to keep the components of the disinfection agent separate until the agent is about to be applied to the surface 2. Just before application thereof, mixing takes place, for example by the use of mixing nozzles or nozzle arrangements that comprise at least one nozzle for each component. If the objects 1 are containers, the mixing nozzles or nozzle arrangements are constituent parts of a treatment position of a machine for the cleaning and/or sterilization of containers, such as a rinsing machine.

Some practices of the method include executing all three steps a-c at one and the same treatment position. In these practices, the object 1 remains at this treatment position until the completion of the method.

Other practices include executing the method steps at different treatment positions. These practices include moving the object 1 from one location to the next as treatment progresses.

For the sake of better overview it has also been assumed that the method steps a-c are carried out in time sequence one after another. However, in some practices, the treatment supporting the effect of the disinfection agent, with the bactericidal treatment medium and/or with the bactericidal energy application, namely the first step a, is carried out simultaneously with the treatment with the disinfection agent, namely step b. In other practices, the first and second steps partially temporally overlap.

The invention has been described heretofore on the basis of exemplary embodiments. It is understood that numerous alterations or deviations are possible without thereby leaving the inventive concept on which the invention is based.

Having described the invention, and a preferred embodiment thereof, what is claimed as new, and secured by Letters Patent is:

1. A method comprising disinfecting a surface of packaging, wherein said surface is selected from the group consisting of a product-critical surface and a filling contents-critical surface, wherein disinfecting said surface comprises executing a first step and executing a second step, wherein executing said first step comprises breaking up one of an outer covering and a membrane of germs on said surface by applying a chlorine compound at a first dosage, and wherein executing said second step comprises applying, to said surface, a disinfection agent that comprises carbon dioxide and said chlorine compound, wherein said chlorine compound in said second step is applied at a second dosage that is less than said first dosage.

2. The method of claim 1, wherein said disinfection agent is applied in liquid form.

3. The method of claim 1, wherein said disinfection agent is applied in gas form.

4. The method of claim 1, wherein said disinfection agent is applied in aqueous form.

5. The method of claim 1, wherein the step of executing said first step comprises, in addition to applying a chlorine compound at a first dosage, illuminating said surface with flashes of UV radiation.

6. The method of claim 1, wherein said second step comprises applying carbon dioxide at a first pressure above ambient pressure and reducing said first pressure to ambient pressure after said carbon dioxide has been applied to said surface.

7. The method of claim 1, wherein the step of executing said first step comprises applying chlorine dioxide at a first dosage.

8. The method of claim 1, further comprising executing said second step only after having executed said first step.

9. The method of claim 1, further comprising beginning execution of said second step before completion of said first step.

10. The method of claim 1, wherein the step of breaking up said one of an outer covering and a membrane of germs on said surface further comprises illuminating with UV radiation.

11. The method of claim 1, wherein the step of breaking up said one of an outer covering and a membrane of germs on said surface further comprises illuminating with ultrasonic radiation.

12. The method of claim 1, wherein said chlorine compound comprises chlorine dioxide.

* * * * *